United States Patent

Kawaguchi

[11] Patent Number: 5,813,852
[45] Date of Patent: Sep. 29, 1998

[54] ORTHODONTIC BRACKET

[75] Inventor: Kozo Kawaguchi, Fukushima Ken, Japan

[73] Assignee: GAC International, Inc., Central Islip, N.Y.

[21] Appl. No.: 458,838

[22] Filed: Jun. 2, 1995

[30] Foreign Application Priority Data

Feb. 17, 1995 [JP] Japan ................................. 7-052040

[51] Int. Cl.⁶ ....................................................... A61C 3/00
[52] U.S. Cl. ................................................ 433/8; 433/10
[58] Field of Search ............................. 433/8, 9, 10, 11, 433/12, 13, 14, 15, 16, 17

[56] References Cited

U.S. PATENT DOCUMENTS

| | | | |
|---|---|---|---|
| 2,908,974 | 10/1959 | Stifter | 32/14 |
| 3,469,314 | 9/1969 | Pearlman | 32/14 |
| 3,765,091 | 10/1973 | Northcutt | 32/14 A |
| 3,775,850 | 12/1973 | Northcutt | 32/14 A |
| 3,922,787 | 12/1975 | Fischer et al. | 433/15 |
| 3,930,311 | 1/1976 | Andrews | 32/14 A |
| 3,964,165 | 6/1976 | Stahl | 32/14 A |
| 4,050,156 | 9/1977 | Chasanoff et al. | 32/2 |
| 4,107,844 | 8/1978 | Kurz | 32/14 A |
| 4,186,488 | 2/1980 | Wallshein | 433/8 |
| 4,249,897 | 2/1981 | Anderson | 433/8 |
| 4,299,569 | 11/1981 | Frantz | 433/8 |
| 4,302,532 | 11/1981 | Wallshein | 433/8 |
| 4,353,692 | 10/1982 | Karrakussoglu | 433/16 |
| 4,674,978 | 6/1987 | Acevedo | 433/8 |
| 4,717,341 | 1/1988 | Goldberg et al. | 433/9 |
| 4,850,865 | 7/1989 | Napolitano | 433/8 |
| 4,894,012 | 1/1990 | Goldberg et al. | 433/215 |
| 5,078,596 | 1/1992 | Carberry et al. | 433/8 |
| 5,141,436 | 8/1992 | Orlowski et al. | 433/226 |
| 5,154,606 | 10/1992 | Wildman | 433/8 |
| 5,254,002 | 10/1993 | Reher et al. | 433/8 |
| 5,318,440 | 6/1994 | Adam et al. | 433/8 |
| 5,358,402 | 10/1994 | Reed et al. | 433/8 |
| 5,380,196 | 1/1995 | Kelly et al. | 433/8 |

FOREIGN PATENT DOCUMENTS

| | | | |
|---|---|---|---|
| 0 316 086 | 5/1989 | European Pat. Off. | A61K 6/08 |
| 0 326 758 | 6/1990 | European Pat. Off. | . |
| 0 476 789 | 3/1992 | European Pat. Off. | A61K 6/083 |
| 41 35 434 | 4/1993 | Germany | A61C 7/12 |
| 43 43 275 | 6/1994 | Germany | A61C 7/12 |

OTHER PUBLICATIONS

*Journal of Clinical Orthodontics*, Mar. 1989; Tella Tech Advertisement.
*Journal of Clinical Orthodontics*, Jan. 1989; Product News Column.
*Journal of Clinical Orthodontics*, Sep. 1986; Mirage bracket advertisement.
*American Journal of Orthodontics*, vol. 89, No. 6 (Jun. 1986); American Orthodontics Advertisement.
*American Journal of Orthodontics and Dentofacial Orthopedics*, vol. 95, No. 5 (May 1989); Silkon Bracket Advertisement.
*Journal of Clinical Orthodontics*, Sep. 1990; Ormco Advertisement.

*Primary Examiner*—Nicholas D. Lucchesi
*Attorney, Agent, or Firm*—Kenyon & Kenyon

[57] ABSTRACT

An orthodontic bracket is provided including a plastic bracket main member (1) having a wire slot (2) and tie-wings (3). A reinforcing member (11) having a retention groove (14) is embedded in the bracket main member (1) such that the wire slot (2) is reinforced by the retention groove (14) of reinforcing member (11). An orthodontic arch wire used in orthodontic treatment is retained by the retention groove (14) of the reinforcing member (11). The reinforcing member (11) also includes a groove (16) delineating a vertical slot for receiving auxiliary apparatuses such as uprighting springs and rotation springs such that orthodontic treatment requiring such apparatuses can be suitably performed using plastic brackets.

46 Claims, 13 Drawing Sheets

ORTHODONTIC BRACKET

FIELD OF THE INVENTION

The present invention relates generally to orthodontic brackets and, more particularly, to improvements in reinforced plastic orthodontic brackets having reinforcing members therein.

BACKGROUND OF THE INVENTION

Prior brackets of this type essentially provide (a) a bracket main member made of resin and having an arch wire slot with one or two pairs of tie-wings and (b) a metal reinforcing member having a U-shaped cross-section and being positioned at the sides of the arch wire slot of the bracket main member.

It is thus possible to reinforce the sides of the arch wire slot of the bracket main member with the use of metal reinforcing members. Accordingly, when tongue forces are applied to the sides of the wire slot by an angular arch wire during orthodontic treatment, the bracket is less likely to break or deform unlike earlier plastic brackets.

However, although these prior brackets reduce breakage and deformation of the wire slots, they do not provide satisfactory reinforcement to areas other than the slot. Moreover, these brackets do not provide vertical slots for retaining auxiliary devices such as uprighting springs and rotation springs, making orthodontic treatment using such auxiliary devices difficult.

SUMMARY OF THE INVENTION

The present invention was developed to effectively resolve the various problems of such prior brackets. The invention is directed to an orthodontic bracket that furnishes (a) a bracket main member made of plastic or resins having a wire slot and tie-wings and (b) a reinforcing member defining a retention groove and a vertical slot. The reinforcing member is positioned in the bracket main member so that the arch wire is retained by the retention groove of the reinforcing member. The vertical slot is provided for retaining auxiliary orthodontic devices.

It is preferred that the groove means for delineating the vertical slot comprise a tube. It is also preferred that extended portions integral with the reinforcing member be provided that extend inside the wings, and further that the extended portions directly engage arch wire ligature means attached to the bracket.

Furthermore, the vertical slot defined by the reinforcing member may be inclined with respect to the longitudinal axis of the wire slot.

Thus, with the present invention, the slot for retaining the arch wire can be defined substantially by only the retention groove of a reinforcing element when the reinforcing element is positioned in the sides of the wire slot of the bracket main member. The reinforcing member also defines the groove-shaped vertical slot, which makes it possible to perform suitable orthodontic treatment using auxiliary apparatus such as uprighting springs and rotation springs, even with plastic brackets.

DETAILED DESCRIPTION

A detailed explanation of the several embodiments of the present invention is set forth below.

Figure 1:
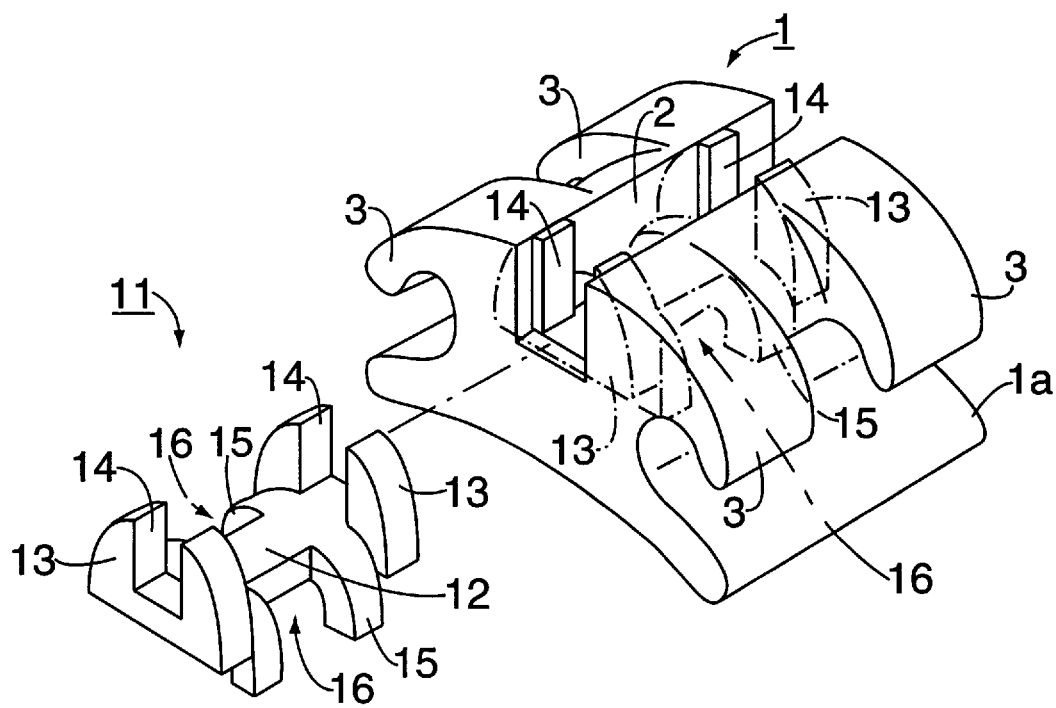
FIG. 1 is a perspective view of an orthodontic bracket with respect to a first embodiment of the present invention illustrating the combination of a bracket main member and a metal reinforcing member.

A bracket in accordance with the first embodiment of the invention is illustrated in FIG. 1. The bracket comprises a resin or plastic bracket main member or bracket body 1 and a metal reinforcing or reinforcement member 11 embedded in the main member 1. The bracket main member 1 includes a U-shaped horizontal wire slot 2 (extending generally in a mesio-distal direction) at the center of the main member. In addition, the main member includes two pairs of tie-wings 3 integrally formed with the end portions and on both sides of the main member for securing arch wire ligature means (not shown in FIG. 1).

The metal reinforcing member 11 may be formed as an integral member by pressing or stamping processes. A pair of upstanding portions 13 having predetermined heights are provided at the edges of both ends of a base portion 12. Also, angular retention grooves 14 each having a width smaller than the width of the horizontal wire slot 2 are formed between upstanding portions 13. A pair of downward hanging portions 15 having predetermined dimensions are provided at the edges of both sides of base portion 12. An angular delineation groove 16 that defines a generally vertical slot (extending generally in a gingival-occlusal direction) is formed between hanging portions 15.

Figure 2A:
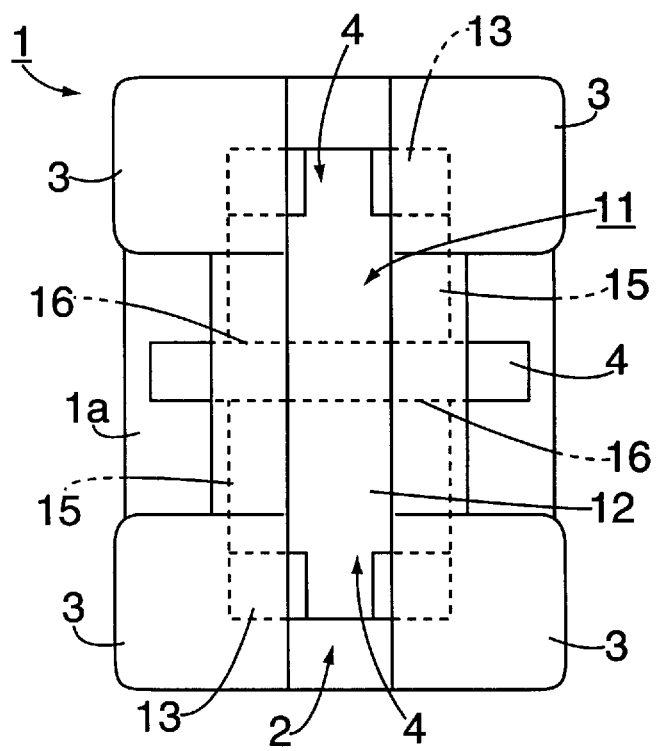
FIG. 2A is a top plan view of the FIG. 1 bracket.
Figure 2B:
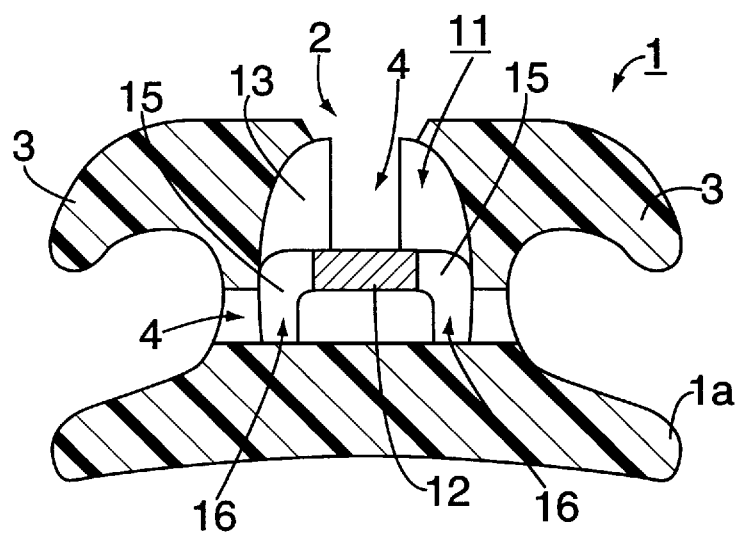
FIG. 2B is a cross-sectional side view of the FIG. 1 bracket taken generally midway through the bracket.

Consequently, when the metal reinforcing element 11 is inserted about the wire slot 2 of the bracket main member 1 with insertion forming or molding methods ordinarily used in this field, the retention grooves 14 formed by the upstanding portions 13 of the metal reinforcing element 11 project slightly inside from the bottom surface and side surfaces of the wire slot 2 as shown in FIGS. 2A and 2B. The retention grooves 14 are substantially the only portion of the bracket that engage the arch wire during orthodontic treatment. At the same time the reinforcing element 11 also continuously delineates a vertical auxiliary appliance receiving slot 4 open at both ends along groove 16 defined by the several hanging portions 15 between the wings 3 and the base 1a of the bracket main member 1. The vertical slot is oriented at a right angle with respect to the wire slot 2 of the bracket main member 1.

Because of the presence of the metal reinforcing element 11 in the bracket of the first embodiment, it is possible to substantially reduce breakage and deformation occurring in earlier plastic brackets when torguing forces are applied to wire slot 2 by an arch wire during orthodontic treatment. In addition, since the arch wire is directly retained inside the slot portion delineated only by the pair of retention grooves 14, there is substantially no contact with the resin slot surfaces of bracket main member 1, making it is possible to smoothly shift the bracket main member 1 along the arch wire when the bracket is affixed to a tooth.

Figure 3A:
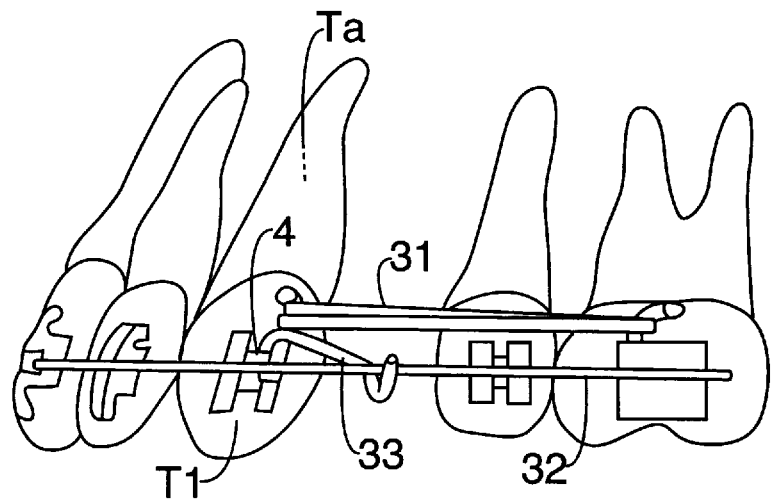
FIG. 3A is a front view of teeth in a dental arch illustrating an example of orthodontic treatment using uprighting springs.

As shown in FIG. 3A, a canine tooth T1 can be shifted in the distal direction using an elastic 31 or a coil spring (not shown) at the center of the tooth. It has been possible to shift the canine tooth T1 parallel to the distal direction without inclining it by inserting and anchoring one end of an uprighting spring 33 inside the vertical slot 4 and hanging the other end on arch wire 32 to utilize its counterforce.

Figure 3B:
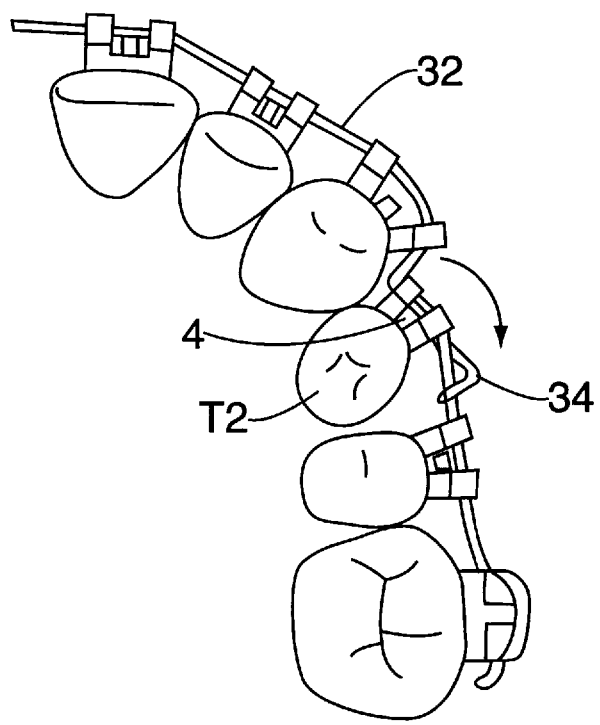
FIG. 3B is a bottom view of teeth in a dental arch illustrating an example of orthodontic treatment using a rotation spring.

Similarly, as shown in FIG. 3B, it is also possible to rotate bicuspid T2 by inserting and anchoring one end of a rotation spring 34 in the vertical slot 4 and hanging the other end on the arch wire 32 to make positive use of the counterforce and use this in the same manner as with earlier metal brackets fitted with vertical slots. It is also possible as a matter of convenience to mount a hook (not shown) in the vertical slot 4 to transform a hookless bracket into a bracket with a hook for use with an elastic 31 or a coil spring.

In addition to the wire slot 2, the vertical slot 4 is strengthened by the reinforcing member 11. In particular, the pair of hanging pieces 15 in the first embodiment reduce breakage or deformation of the vertical slot 4 even when using such auxiliary appliances as uprighting springs 33 and rotation springs 34 and hooks.

Figure 4A:
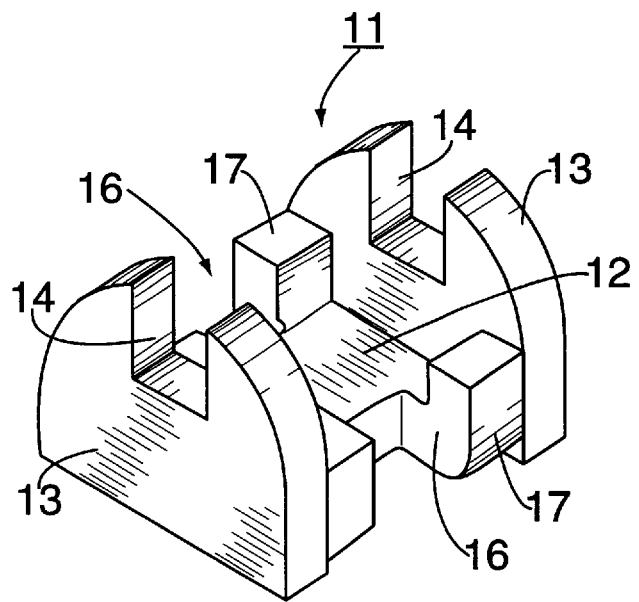
FIG. 4A is a perspective view of a modified metal reinforcing member relating the first embodiment.
Figure 4B:
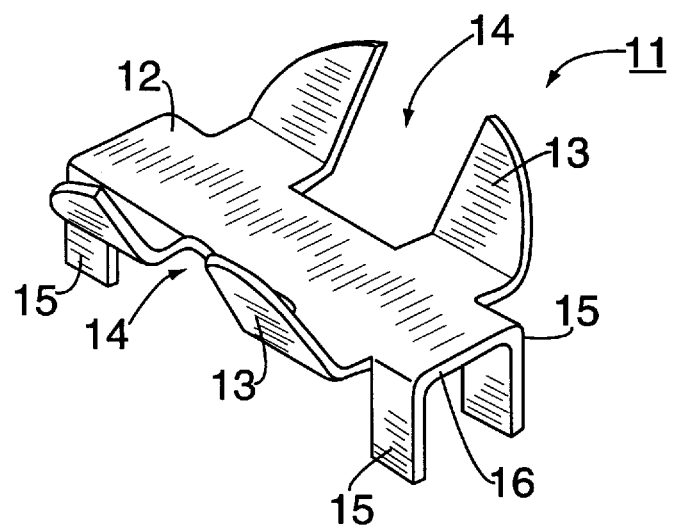
FIG. 4B is a perspective view of another modified metal reinforcing member relating the first embodiment.

The metal reinforcing member 11 of the first embodiment may be made, for example, in one of the following ways depending on particular requirements. As shown in FIG. 4A, the member 11 may be made by forming the delineated groove 16 that defines the vertical slot 4 between pair of short upstanding portions 17 by increasing the heights of the pair of upstanding portions 13 at both ends of the base 12 and providing pairs of shorter upstanding portions 17 at both ends of the base 12. Or as shown in FIG. 4B, the member 11 may be made by furnishing hanging pieces 15 that hang down from both ends of the base 12 together with furnishing pairs of upstanding portions 13. The upstanding portions 13 are inclined so that they form retention grooves 14 in the central portions of both side edges of the base 12 from their upper ends to their roots where they are attached, so that they form an angular delineated grooves 16 that define the vertical slot 4 between the hanging portions 15 that are present in opposite positions on each end of the base 12.

Figure 5:
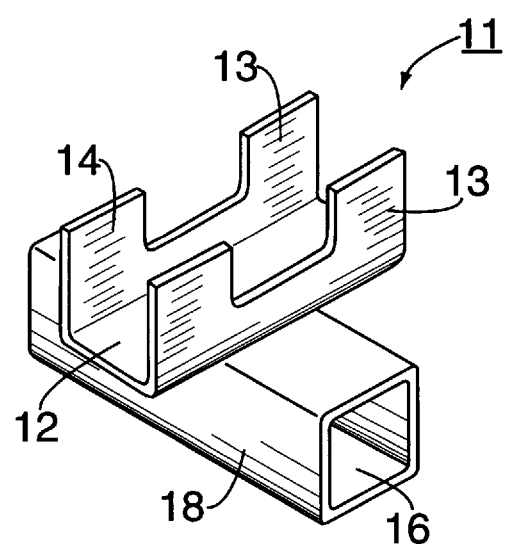
FIG. 5 is a perspective view of a metal reinforcing member provided with respect to a second embodiment of the invention.

A second embodiment of a bracket in accordance with the invention is described below. Unlike the first embodiment where pairs of upstanding portions 13 are furnished to form an angular retention groove 14 on both ends of the base portion 12, here as shown in FIG. 5, a pair of upstanding portions 13 are formed continuously over the entire length of both sides of the base portion 12 to utilize all of the space between the continuous upstanding portions 13 as the retention groove 14. In addition, an angular tube 18 is soldered or welded to the lower surface of the base portion 12 to delineate a groove 16 defining vertical slot 12. In this case, it is also possible to use tubes of other configurations such as round tubes instead of the angular tube 18.

Although not specifically illustrated here with the second embodiment brackets, when the metal reinforcing member 11 of the second example has been inserted into the sides of the wire slot 2 of the bracket main member 1 by manufacturing methods commonly used in the art, the base portions 12 and the upstanding portions 13 of the metal reinforcing element 11 project considerably inside the wire slot 2 from the bottom surface and both side surfaces so as to continuously delineate the slot portion that retains the arch wire. At the same time, a vertical slot 4 is formed continuously along the inside of the angular tube 18 between the wings 3 and the base 1a and intersecting at certain angles with the wire slot 2 of the bracket main member 1.

Figure 6A:
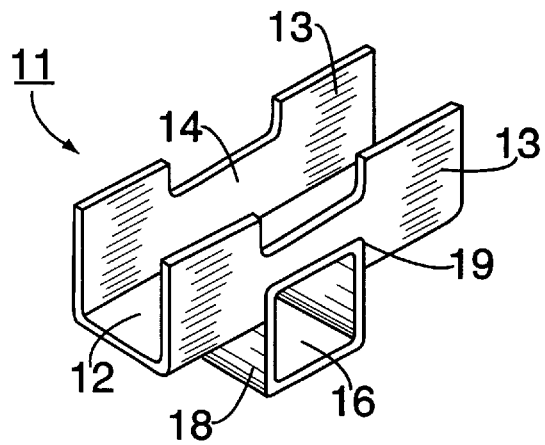
FIGS. 6A, 6B and 6C are perspective views of various modified metal reinforcing members relating to the second embodiment.
Figure 6B:
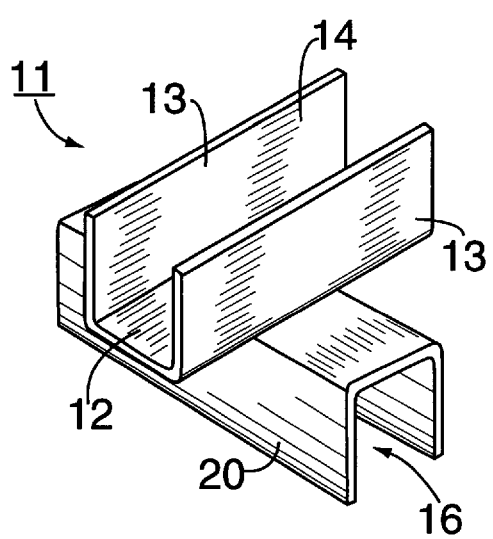
Figure 6C:
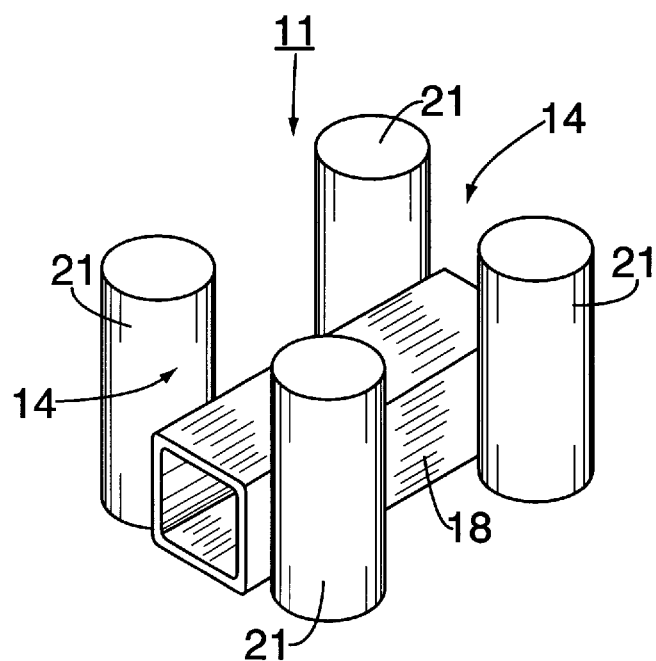

It is possible to make various modifications to the metal reinforcing element 11 of the second embodiment. As shown in FIG. 6A, it is possible to form a concave or recessed portion 19 on the bottom surface of base portion 12. Then, rather than securing the angular tube 18 by soldering or welding processes to the surface of the base portion 12, it is possible to force fit the angular tube 18, whose short dimension equals the width of the retention groove 14, into the concave portion 19. Or as shown in FIG. 6B, it is possible to secure a groove forming element 20, whose section is a reverse U-shape, onto the side of a base portion 12 by soldering or welding methods. Thus, instead of using an angular tube 18, this reverse U-shaped groove forming element 20 can be used as a groove means for delineating the vertical slot 4. Or as shown in FIG. 6C, when using an angular tube 18, it is possible to attach two pairs of round rods 21 by soldering or welding processes to each end on both sides of the angular tube 18 in order to delineate a retention groove 14 between the round rods 21 that is somewhat smaller than the width of wire slot 2.

Figure 7A:
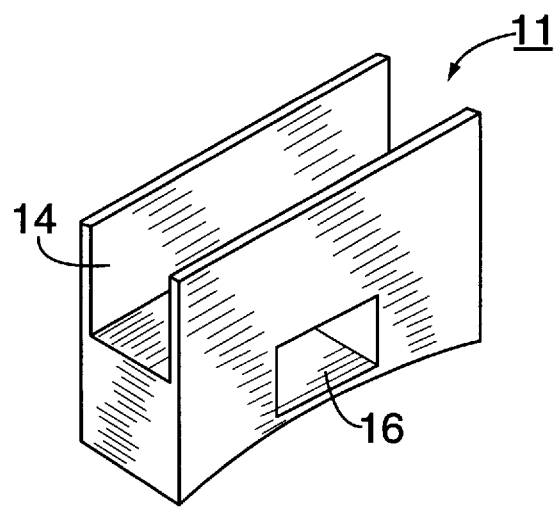
FIGS. 7A and 7B are perspective views of other modified metal reinforcing members relating to the second embodiment.
Figure 7B:
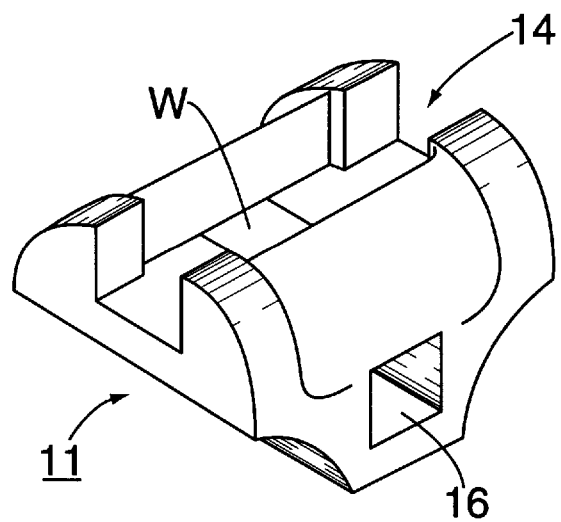
Figure 8A:
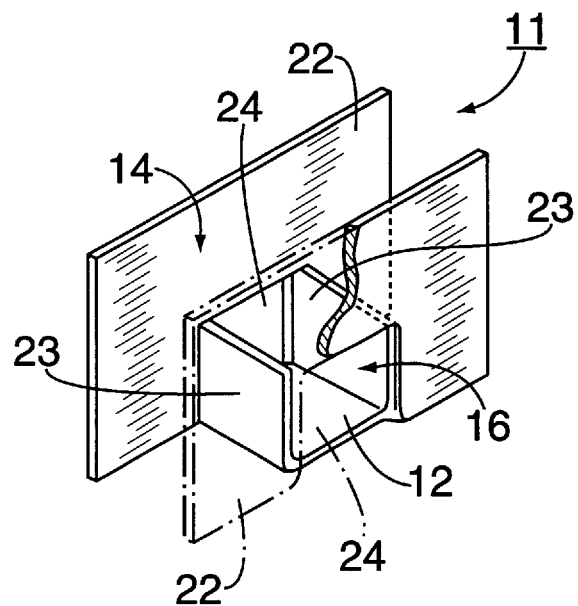
FIGS. 8A and 8B are perspective views of additional modified metal reinforcing members relating to the second embodiment.
Figure 8B:
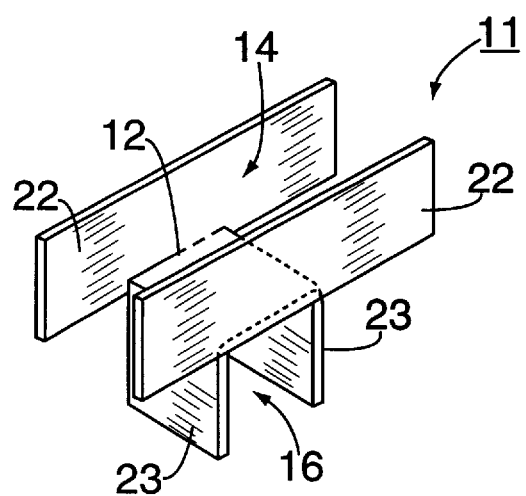

In these cases, the angular tube 18 or the sectional reverse U-shaped groove forming element 20 may be lengthened so that their openings on both sides are exposed at the sides of the bracket main member 1. FIGS. 7A and 7B illustrate other modifications wherein the metal reinforcing member 11 is integrally formed by metal injection molding. The delineated groove 16 and retention groove 14 intersect at certain angles forming a connecting window W or opening at the place of intersection. Or as shown in FIG. 8A, it is possible to punch out a square metal plate to form a pair of large folds 22 and a pair of small folds 23, to cut openings 24 on the periphery of the base portion 12, and then fold the large and small folded portions 22 and 23 upward in order to delineate a retention groove 14 that runs between the pair of large fold portions 22 and to delineate a channel 16 between the pair of small folded pieces 23 that connects to each of the openings 24. Or conversely as shown in FIG. 8B, it is possible to obtain similar results by a construction where the groove 16 is delineated between the small folded portions 23 by folding the pair of small folded portions 23 downward this time instead of cutting openings 24 in the side of the large folded portions 22.

Figure 9:
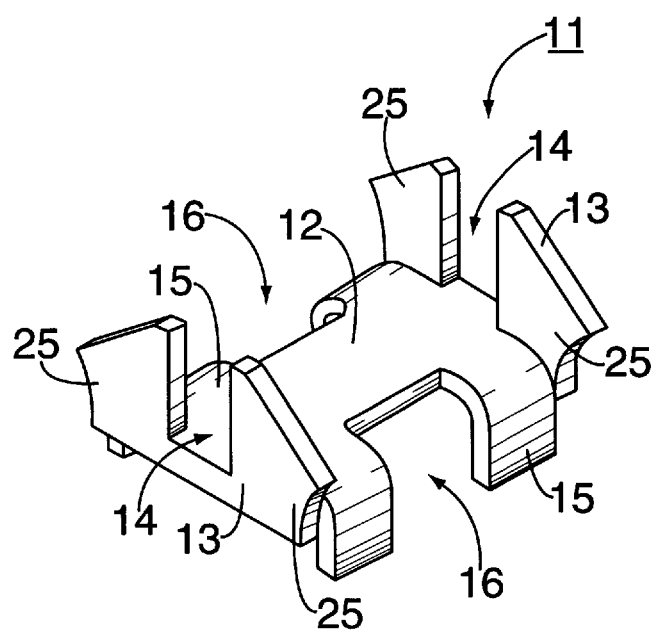
FIG. 9 is a perspective view of a metal reinforcing member provided with respect to a third embodiment of the invention.

The bracket relating to the third embodiment described below is similar in construction to that of the first embodiment but differs in being constructed with emphasis on strengthening the sides of the pair of tie-wings 3 of the bracket. As shown in FIG. 9, the bracket of the third embodiment is characterized by extended portions 25 that project inside each wing 3 at the edges of both sides. The extended portions are formed integrally on the pair of upstanding portions 13, which extend from the edges of both sides of the base portion 12 of the metal reinforcing member 11, to conform with the shapes of the tie-wings 3.

Figure 10A:
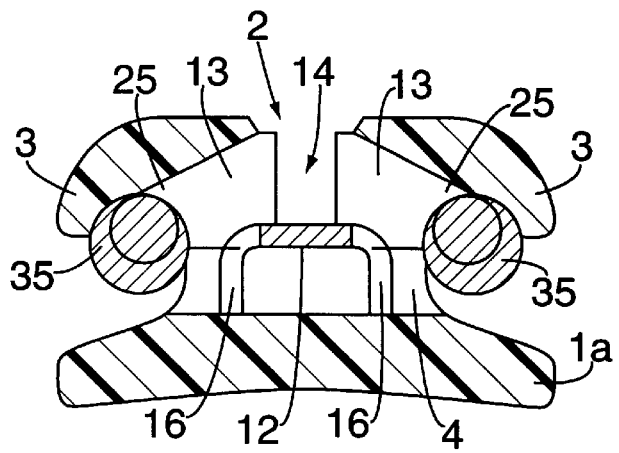
FIG. 10A is a cross-sectional side view of an orthodontic bracket containing the FIG. 9 reinforcing member.

Consequently with the bracket of the third embodiment, when the metal reinforcing member 11 is inserted into the sides of the wire slot 2 of the bracket main member 1 using methods commonly used in the art, the retention groove 14 formed by each upstanding portion 13 of the metal reinforcing member 11 projects considerably inside from the bottom surface and both side surfaces of the wire slot 2 as shown in FIG. 10A in the same manner as in the first embodiment. Thus, a slot portion is formed that retains the arch wire by substantially only the retention groove 14. At the same time, there is a continuous vertical slot 4 that is open at both ends and runs along the delineated groove 16 of each hanging portion 15 between the wings 3 and base 1a and that is perpendicular to the wire slot 2 of the bracket main member 1.

With the bracket of the third embodiment, it is possible to reduce breakage or deformation of the tie-wings 3 that may occur when ligature means 35 are fastened around the lower surfaces of the wings 3 because the sides of the wings 3 are reinforced by the extended portions 25, which are located at the edges of both ends of the pair of upstanding portions 13.

Figure 10B:
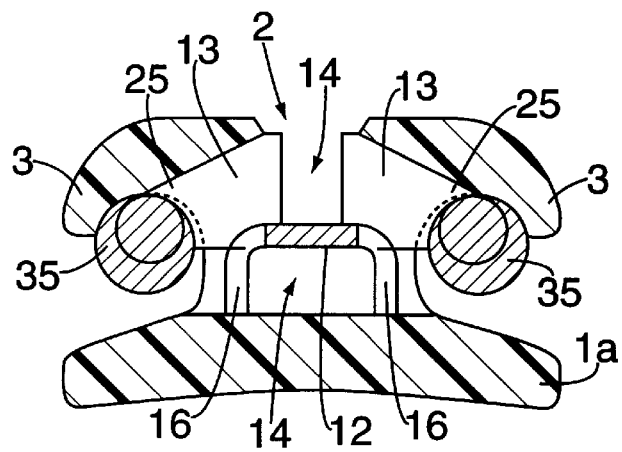
FIG. 10B is a cross-sectional side view of a modification to the orthodontic bracket of FIG. 10A.
Figure 10C:
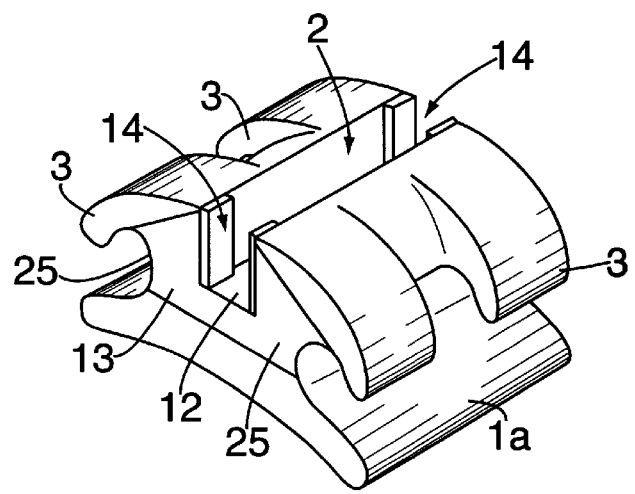
FIG. 10C is a perspective view of a further modification to the orthodontic bracket of FIG. 10A.

Also in this case, it is possible as shown in FIG. 10B to project the edges of the tips of each extended portion 25 outwardly from the outer surfaces of the bracket main member 1 so as to engage ligature means 35 directly on the projecting tips of the said extended portions 25. Or it is possible as shown in FIG. 10C to reinforce the sides of the wings 3 to a far greater extent by positioning the upstanding portions 13 such that they are exposed at the mesio-distal side surfaces of bracket main member 1.

Figure 11:
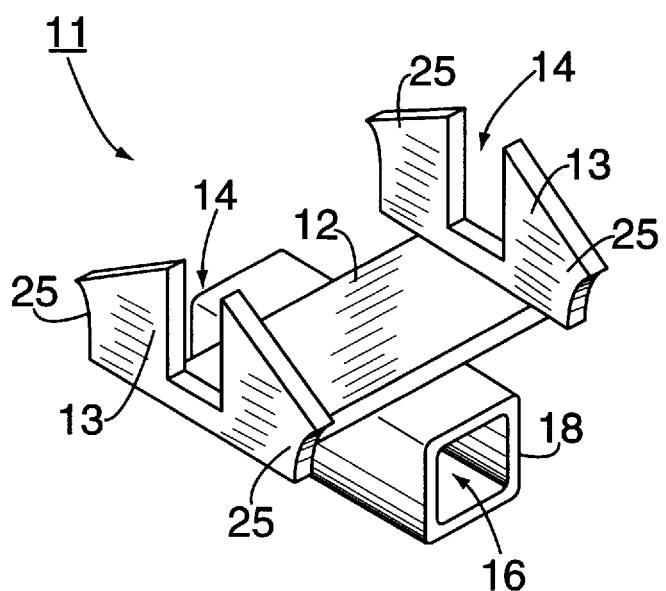
FIG. 11 is a perspective view of a modified metal reinforcing member relating to the third embodiment of the invention.

The metal reinforcing member 11 relating to the third embodiment can be modified to use round tubes or an angular tube 18 as shown in FIG. 11, without limit to what has been illustrated.

Figure 12A:
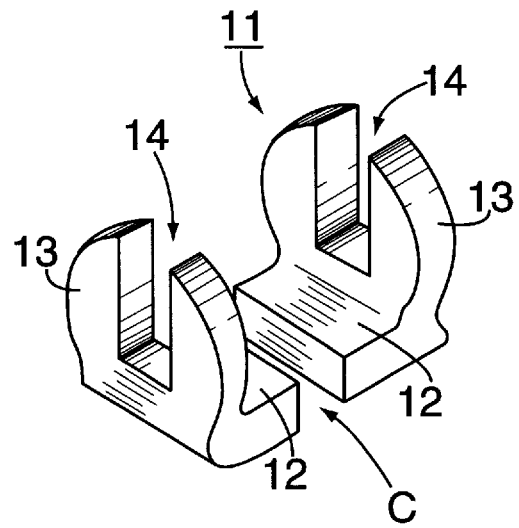
FIG. 12A is a perspective view of a metal reinforcing member with respect to a fourth embodiment of the invention.

A bracket relating to the fourth embodiment described next is similar to that of the first embodiment but differs as shown in FIG. 12A in that it includes a groove defining a vertical slot 4 formed in a partition region C by dividing the base portion 12 of metal reinforcing member 11 at its center into two equal right and left parts. Also, the hanging portions 15 that formed delineated groove 16 of the first embodiment are eliminated.

Figure 12B:
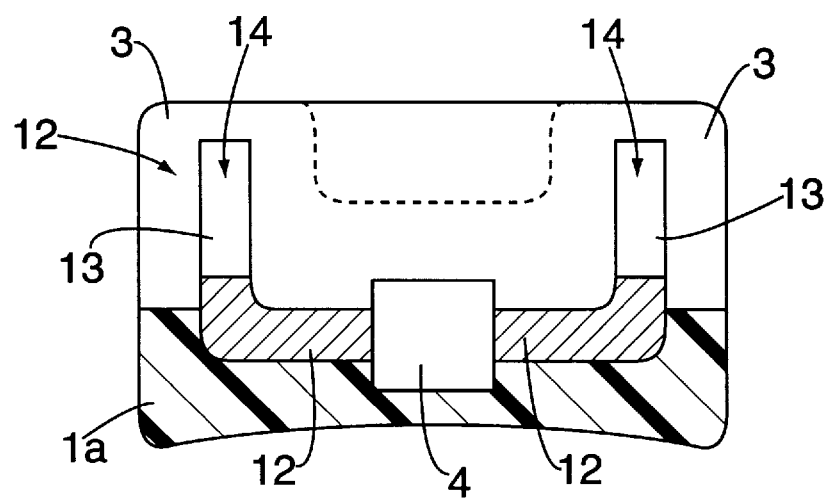
FIG. 12B is a cross-sectional front view of an orthodontic bracket containing the metal reinforcing member of FIG. 12A.

Consequently, when the partitioned metal reinforcing member 11 of the bracket of the fourth embodiment is inserted into the sides of wire slot 2 of bracket main member 1 at a prescribed interval as shown in FIG. 12B, the retention grooves 14 formed by the upstanding portions 13 of the partitioned metal reinforcing member 11 project considerably inside from the bottom surface and both side surfaces of the wire slot 2 so as to delineate the slot portion that actually retains the arch wire substantially by the retention grooves 14 only. At the same time, the vertical slot 4 open at both ends and extending inside the partition region or gap C is continuously delineated between the wings 3 and the base 1a at right angles to the wire slot 2 of the bracket main member 1.

Figure 13:
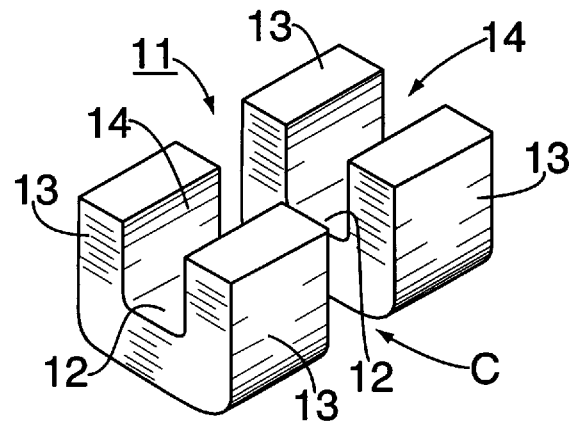
FIG. 13 is a perspective of a modified metal reinforcing member relating to the fourth embodiment of the invention.

Further in this case as shown in FIG. 13, it is possible to form the metal reinforcing member 11 with a pair of upstanding portions 13 having a continuous sectional U-shape on the edges of both sides of the base portion 12. The sectional U-shaped metal reinforcing member 11 can then be partitioned so as to divide it in two at its center, thereby using the partition region C in the same manner to delineate a vertical slot 4.

Figure 14:
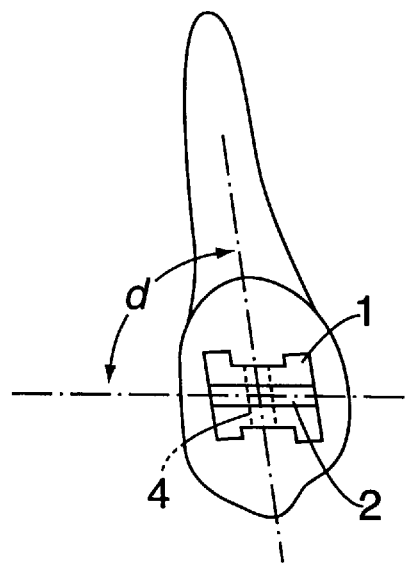
FIG. 14 is a front view of a tooth with a bracket mounted thereon illustrating the inclination of the vertical slot of the bracket relative to the arch wire slot.

Although the embodiments described above include a vertical slot 4 that intersects the wire slot 2 at right angles, the present invention is not to be delimited thereby. Depending on the objectives of the particular orthodontic treatment required, it is also possible to make various modifications to groove shapes and groove means furnished in each of the metal reinforcing members 11. It is also possible to orient the vertical slot 4 at any desired inclined angle (for example, from 70° to 110°) as shown in FIG. 14, relative to the longitudinal axis of the wire slot 2.

Furthermore, the effect on the aesthetics of transparent or semitransparent brackets will be minimized when any of the exemplified metal reinforcing members 11 are whitened by methods such as plating or coating. Also, the metal reinforcing members 11 can be formed by casting or machining methods and the like in addition to the stated stamping and metal injection forming processes. Moreover, if the surfaces of the member 11 are roughened to include minute unevenness during forming or thereafter, their bonding to bracket main members 1 will be improved, reducing the possibility of inadvertent separation of the member 1 and the member 11.

Still further, while it is preferred to form the reinforcing members 11 out of metal materials as stated in the examples, it is also possible to form the members from other materials such as plastics, glass and ceramics provided they are sufficiently hard and have a suitable static friction coefficient.

By adopting the teachings of the present invention as described above, it is possible to provide a strengthened vertical slot in plastic brackets in which reinforcing members are inserted. This makes it possible to perform suitable orthodontic treatment using auxiliary apparatus or appliances such as uprighting springs and rotation springs.

In addition, the reinforcing member can include extended portions that project inside the tie-wings of the bracket and directly engage arch wire ligature means tied on the bracket. The sides of the wire slot, the vertical slot and the tie-wing sides are therefore strengthened, making it possible to further increase the practical use of plastic brackets having superior aesthetic characteristics.

Because the reinforcing member has a groove shape for delineating a vertical slot in addition to the retention groove forming the effective slot for the arch wire, the areas of contact between the reinforcing member and the resin plastic main member are numerous, reducing the possibility of the reinforcing member slipping out of position after insertion.

I claim:

1. An orthodontic bracket for use in orthodontic treatment with an arch wire and an auxiliary orthodontic appliance, comprising:

a plastic bracket body including a slot therein; and a reinforcement member embedded in said bracket body, said reinforcement member defining a wire retention slot located in said slot of said bracket body for receiving and engaging the arch wire, said reinforcement member also defining an auxiliary appliance slot configured for receiving and retaining the auxiliary appliance therein.

2. The orthodontic bracket of claim 1, wherein said bracket body includes tie wings extending from opposite sides of said bracket body slot, and wherein said reinforcement member includes extensions projecting into said tie wings to reinforce said tie wings.

3. The orthodontic bracket of claim 2, wherein said extensions project beyond outer surfaces defining said tie wings such that ligature means affixed to said orthodontic bracket are engaged by said extensions.

4. The orthodontic bracket of claim 1, wherein said reinforcement member includes a tube defining said auxiliary appliance slot.

5. The orthodontic bracket of claim 4, wherein said tube includes planar internal surfaces.

6. The orthodontic bracket of claim 4, wherein said tube is round.

7. The orthodontic bracket of claim 1, wherein said bracket body slot extends substantially along a mesio-distal axis of the bracket, and wherein said auxiliary appliance slot extends along an axis substantially perpendicular to said axis of the bracket body slot.

8. The orthodontic appliance of claim 1, wherein said auxiliary appliance slot is inclined with respect to said bracket body slot.

9. The orthodontic bracket of claim 1, wherein said reinforcement member includes a base portion and at least two downward projections extending from said base portion to define said auxiliary appliance slot.

10. The orthodontic bracket of claim 1, wherein said reinforcement member includes a base portion and a plurality of upstanding projections extending from said base portion to define said wire retention slot.

11. The orthodontic bracket of claim 1, wherein surfaces defining said retention slot are spaced apart from surfaces defining said bracket body slot, such that said retention slot engages the arch wire and substantially reduces contact between the arch wire and said surfaces defining said bracket body slot.

12. The orthodontic bracket of claim 1, wherein said reinforcement member comprises a material harder than the plastic bracket body.

13. The orthodontic bracket of claim 1, wherein said reinforcement member comprises metal.

14. The orthodontic bracket of claim 1, wherein said reinforcement member comprises two spaced-apart portions having a gap therebetween, each including a part of said retention slot, and wherein said auxiliary appliance slot is defined by the gap between said portions.

15. The orthodontic bracket of claim 1, wherein said reinforcement member is whitened.

16. The orthodontic bracket of claim 1, wherein said plastic bracket body contains filler for hardening said bracket body.

17. The orthodontic bracket of claim 1, wherein said plastic bracket body is translucent.

18. The orthodontic bracket of claim 1, wherein said plastic bracket body is transparent.

19. An orthodontic bracket for use with an arch wire and an auxiliary orthodontic appliance, comprising:

a plastic bracket body including a slot therein, said slot having an axis extending substantially along a mesio-distal direction; and a metal reinforcement member embedded in said bracket body, said reinforcement member including a wire retention slot located in said slot of said bracket body for receiving and engaging the arch wire such that the arch wire substantially avoids contact with said bracket body, said reinforcement member also including an auxiliary appliance slot positioned in said bracket body and configured for receiving and retaining the auxiliary appliance therein.

20. The orthodontic bracket of claim 19, wherein said bracket body includes tie wings extending from opposite sides of said bracket body slot, and wherein said reinforcement member includes extensions projecting into said tie wings to reinforce said tie wings.

21. The orthodontic bracket of claim 20, wherein said extensions project beyond outer surfaces defining said tie wings such that ligature means affixed to said orthodontic bracket are engaged by said extensions.

22. The orthodontic bracket of claim 19, wherein said reinforcement member includes a tube defining said auxiliary appliance slot.

23. The orthodontic bracket of claim 22, wherein said tube includes planar internal surfaces.

24. The orthodontic bracket of claim 22, wherein said tube is round.

25. The orthodontic bracket of claim 19, wherein said auxiliary appliance slot extends along an axis substantially perpendicular to said axis of the bracket body slot.

26. The orthodontic bracket of claim 19, wherein said auxiliary appliance slot is inclined, with respect to said bracket body slot.

27. The orthodontic bracket of claim 19, wherein said reinforcement member includes a base portion and at least two downward projections extending from said base portion to define said auxiliary appliance slot.

28. The orthodontic bracket of claim 19, wherein said reinforcement member includes a base portion and a plurality of upstanding projections extending from said base portion to define said wire retention slot.

29. The orthodontic bracket of claim 19, wherein said reinforcement member comprises two spaced-apart portions having a gap therebetween, each including a part of said retention slot, and wherein said auxiliary appliance slot is defined by the gap between said portions.

30. The orthodontic bracket of claim 19, wherein said reinforcement member is whitened.

31. The orthodontic bracket of claim 19, wherein said plastic bracket body contains filler for hardening said bracket body.

32. The orthodontic bracket of claim 19, wherein said plastic bracket body is translucent.

33. The orthodontic bracket of claim 19, wherein said plastic bracket body is transparent.

34. An orthodontic bracket for use in orthodontic treatment with an arch wire and an auxiliary orthodontic appliance, comprising:

a plastic bracket body including a slot therein, said bracket body being translucent and including a filler therein to increase hardness thereof; and a metal reinforcement member fixed in said bracket body, said reinforcement member defining a wire retention slot positioned in said slot of said bracket body for receiving and engaging the arch wire such that contact between the arch wire and the bracket body is inhibited, said reinforcement member also defining an auxiliary appliance slot configured for receiving and retaining the auxiliary appliance therein.

35. The orthodontic bracket of claim 34, wherein said bracket body includes tie wings extending from opposite sides of said bracket body slot, and wherein said reinforcement member includes extensions projecting into said tie wings to reinforce said tie wings.

36. The orthodontic bracket of claim 35, wherein said extensions project beyond outer surfaces defining said tie wings such that ligature means affixed to said orthodontic bracket are engaged by said extensions.

37. The orthodontic bracket of claim 34, wherein said reinforcement member includes a tube defining said auxiliary appliance slot.

38. The orthodontic bracket of claim 37, wherein said tube includes planar internal surfaces.

39. The orthodontic bracket of claim 37, wherein said tube is round.

40. The orthodontic bracket of claim 34, wherein said bracket body slot extends substantially along a mesio-distal axis of the bracket, and wherein said auxiliary appliance slot extends along an axis substantially perpendicular to said axis of the bracket body slot.

41. The orthodontic appliance of claim 34, wherein said auxiliary appliance slot is inclined with respect to said bracket body slot.

42. The orthodontic bracket of claim 34, wherein said reinforcement member includes a base portion and at least two downward projections extending from said base portion to define said auxiliary appliance slot.

43. The orthodontic bracket of claim 34, wherein said reinforcement member includes a base portion and a plurality of upstanding projections extending from said base portion to define said wire retention slot.

44. The orthodontic bracket of claim 34, wherein said reinforcement member comprises two spaced-apart portions having a gap therebetween, each including a part of said retention slot, and wherein said auxiliary appliance slot is defined by the gap between said portions.

45. An orthodontic bracket for use in orthodontic treatment with an arch wire and an auxiliary orthodontic appliance, comprising:

a plastic bracket body including a slot therein, said bracket body being transparent and including a filler therein to increase hardness thereof; and a metal reinforcement member fixed in said bracket body, said reinforcement member defining a wire retention slot positioned in said slot of said bracket body for receiving and engaging the arch wire such that contact between the arch wire and the bracket body is inhibited, said reinforcement member also defining an auxiliary appliance slot configured for receiving and retaining the auxiliary appliance therein.

46. An orthodontic bracket for use in orthodontic treatment with an arch wire and an auxiliary orthodontic appliance, comprising:

a plastic bracket body including a slot extending generally in a mesial-distal direction and an opening extending generally in a gingival-occlusal direction; and a reinforcement member embedded in said bracket body, said reinforcement member defining a wire retention slot located in said slot of said bracket body for receiving and engaging the arch wire, said reinforcement member also defining an auxiliary appliance slot at said opening for receiving and retaining the auxiliary appliance.

* * * * *